(12) United States Patent
Loskutoff et al.

(10) Patent No.: US 7,674,576 B2
(45) Date of Patent: Mar. 9, 2010

(54) SEMEN EXTENDER COMPOSITION AND METHODS FOR MANUFACTURING AND USING

(75) Inventors: Naida M. Loskutoff, Bellevue, NE (US); Jennifer Rohr, Crete, NE (US); Richard B. Lomneth, Omaha, NE (US); David G. Wood, Omaha, NE (US); Elizabeth Crichton, Omaha, NE (US)

(73) Assignee: ABS Corporation, Omaha, NE (US)

( * ) Notice: Subject to any disclaimer, the term of this patent is extended or adjusted under 35 U.S.C. 154(b) by 0 days.

(21) Appl. No.: 10/044,796

(22) Filed: Jan. 11, 2002

(65) Prior Publication Data

US 2003/0186212 A1 Oct. 2, 2003

Related U.S. Application Data

(60) Provisional application No. 60/261,528, filed on Jan. 12, 2001.

(51) Int. Cl.
*A01N 1/02* (2006.01)
*A61B 17/43* (2006.01)

(52) U.S. Cl. .............................. 435/2; 435/1.1; 600/33; 600/35

(58) Field of Classification Search ...................... 435/2, 435/404
See application file for complete search history.

(56) References Cited

U.S. PATENT DOCUMENTS

| | | | |
|---|---|---|---|
| 3,185,623 A | 5/1965 | Smith et al. | |
| 3,444,039 A | 5/1969 | Rajamannan | |
| 3,718,740 A | 2/1973 | Hafs et al. | |
| 3,766,008 A | 10/1973 | Macomber | |
| 3,973,003 A | 8/1976 | Colas | |
| 4,267,268 A | 5/1981 | Nelson, Jr. | |
| 4,329,337 A | 5/1982 | Sexton | |
| 4,699,789 A | 10/1987 | Schultz | |
| 5,071,741 A | 12/1991 | Brockbank | |
| 5,580,714 A | 12/1996 | Polovina | |
| 5,879,877 A | 3/1999 | Ellington et al. | |
| 5,897,987 A | 4/1999 | Oliver et al. | |
| 5,910,568 A | 6/1999 | Hammerstedt et al. | |
| 5,972,592 A | 10/1999 | Suarez | |
| 5,983,661 A | 11/1999 | Wiesman | |
| 6,071,689 A | 6/2000 | Seidel et al. | |
| 6,130,034 A | 10/2000 | Aitken | |
| 6,140,121 A * | 10/2000 | Ellington et al. ............. 435/374 |
| 6,368,786 B1 * | 4/2002 | Saint-Ramon et al. ......... 435/2 |
| 6,641,853 B1 * | 11/2003 | Kowata et al. ............... 426/332 |

FOREIGN PATENT DOCUMENTS

EP 0 685 556 A1 12/1995

OTHER PUBLICATIONS

Merck Index. 12*th* edition. 1996, p. 1664.*
ATCC Catalogue. ATCC Cell Lines and Hybridomas. 8*th* edition. 1994, p. 552.*
Rota et al. "Fertility after vaginal or uterine deposition of semen frozen in a tris extender with or without STM Paste". Theriogenology, (Apr. 15, 1999) vol. 51, No. 6, pp. 1045-1058.*
Helleman, C. et al., "Tiefgefrierkonservierung von Kaninchensperma. Einfluß eines oberflackenktiven Praparates auf die Befruchtungsfahigkeit", Zuchthyg, No. 23, pp. 33-37 (1988).
Hellemann, C. et al., "Efecto de un surfactante sobre la integridad de espermatozoides ovinos crioconservados", Arch. Med. Vet. XXIX, No. 1, pp. 153-160 (1997).
"Biladyl® Data Sheet", Minitü b GmbH—Germany, 1 page (the data sheet was available prior to Jan. 12, 2001).

* cited by examiner

*Primary Examiner*—Vera Afremova
(74) *Attorney, Agent, or Firm*—Merchant & Gould, P.A.

(57) ABSTRACT

A semen extender composition is provided. The semen extender composition includes a sperm cell protecting amount of phospholipid, an effective amount of surfactant to reduce ice crystal formation during freezing of the composition; a carbohydrate, and a biological buffer to provide a semen extender use solution having a pH of between about 6.9 and about 7.5, and wherein the use solution exhibits an osmolality of about 250 mOsM to about 350 mOsM. Methods for manufacturing and using a semen extender composition are provided.

15 Claims, 4 Drawing Sheets

SEMEN EXTENDER COMPOSITION AND METHODS FOR MANUFACTURING AND USING

This application claims priority to U.S. Provisional Application Ser. No. 60/261,528, filed on Jan. 12, 2001, which is incorporated herein.

FIELD OF THE INVENTION

The invention relates to a semen extender composition and to methods for manufacturing and using a semen extender composition.

BACKGROUND OF THE INVENTION

Semen for artificial insemination is often preserved by freezing. Freezing semen is an effective preservation method, but there is a problem with maintaining potency after thawing. Semen extender compositions are frequently used to preserve the viability of the sperm after thaw.

Many semen extender compositions utilize egg yolk. See, for example, U.S. Pat. No. 6,130,034 to Aitken; U.S. Pat. No. 3,444,039 to Rajamannan; U.S. Pat. No. 3,718,740 to Hafs et al.; and U.S. Pat. No. 3,973,003 to Kolas. A commercial semen extender composition that utilizes raw egg yolk is available under the name Biladyl® from Minitube GmbH. In general, the egg yolk is added to the composition just prior to the addition of the semen.

Attention has focused on providing sperm extender compositions that do not include egg yolk. For example, see U.S. Pat. No. 6,140,121 to Ellington et al. and European Patent No. EP 685 556.

SUMMARY OF THE INVENTION

A semen extender composition is provided according to the invention. The semen extender composition includes a sperm cell protecting amount of phospholipid, an effective amount of surfactant to reduce ice crystal formation during freezing of the composition, a carbohydrate, and a biological buffer to provide a semen extender use solution having a pH of between about 6.9 and about 7.5, and wherein the use solution exhibits an osmolality of about 250 mOsM to about 350 mOsM. The phospholipid can be provided from a non-animal source or an animal source.

A method for using a semen extender composition is provided by the invention. The method includes a step of introducing ejaculate into a semen extender composition to provide a cryogenic solution. The ejaculate can be introduced into the semen extender composition as a raw ejaculate or as a buffered ejaculate. In general, a raw ejaculate is the ejaculate obtained directly from an animal. A buffered ejaculate is a combination of buffering solution and raw ejaculate. The cryogenic solution can then be cooled to provide a frozen solution, and the frozen solution can be thawed to provide a thawed solution. In addition, sperm cells can be recovered from the thawed solution and washed.

A method for manufacturing a semen extender composition is provided by the invention. The method includes a step of mixing semen extender composition components together to form a semen extender composition. A freeze agent can be added during or after the step of mixing but before an ejaculate is added, or a freeze agent can be added after an ejaculate is added to the semen extender composition. Exemplary freeze agents that can be used include glycerol and dimethylsulfoxide.

DETAILED DESCRIPTION OF THE INVENTION

A semen extender composition is provided by the invention. The semen extender composition can include components derived from an animal source and/or the semen extender composition can include components derived from a non-animal source. In one embodiment of the invention, the semen extender composition can be characterized as substantially free of components derived from an animal source. It should be understood that "substantially free" means the extender contains less than about 0.1 wt. % of a component derived from an animal source. In another embodiment of the invention, the semen extender composition can be free of any component derived from an animal source. In a further embodiment of the invention, the semen extender composition can include a component or components that are derived from an animal and these components can be present in the semen extender composition in amounts greater than 0.1 wt. % based on the weight of the semen extender composition. It should be understood that the characterization of the semen extender composition as including or not including components derived from an animal source is not meant to reflect the semen or ejaculate which is added to the semen extender composition.

It is believed that animal products conventionally used in semen extender compositions, such as egg yolk, may contain nonpathogenic organisms or pathogenic organisms harmful to the host or cells provided in contact with the animal product. Although an embodiment of the invention allows for a component or components derived from an animal source, at least one of the embodiments of the invention provides a semen extender composition that does not contain egg yolk or other raw animal product. Semen that can be preserved by the semen extender composition of the invention includes semen from domesticated animals such as bovine, wild cattle and buffalo, endangered species, humans, etc.

The semen extender composition can be provided as a concentrate or as a ready-to-use use solution. When provided as a concentrate, water can be added to provide a use solution. When provided as a use solution, the semen extender composition can be used without any modification. That is, there is no need to add additional water to the composition. The ejaculate can be added directly to the use solution or can be buffered and then added to the use solution. It is expected that a preferred application of the semen extender composition provides for the buffering of an ejaculate, and then adding the buffered ejaculate to the use solution. The volume ratio of buffered ejaculate to use solution is preferably selected to provide a desired level of viability of sperm after thaw. The volume ratio of buffered ejaculate to use solution can be between about 0.7:1 and about 1:1.3, can be between about 0.9:1 and about 1:1.1, and can be about 1:1.

The following discussion identifying ranges of components of the semen extender composition are provided for the use solution unless identified differently. In addition, it should be understood that the term "wt. %" refers to the weight percent of a component based upon the volume of the composition. In addition, the ranges identified support the ranges with and without the word "about" preceding a particular value.

The semen extender composition use solution includes a sufficient amount of water to provide a desired osmolality to help maintain the viability of the cells. If there is too little water, it is believed that the osmolality will become too high. Accordingly, it is expected that the use solution will include at least about 90 wt. % water. If the use solution contains too much water, it is believed that the osmolality will become too low. Accordingly, it is expected that the use solution will include less than about 95 wt. % or less water. In general, it is preferable to keep the osmolality of the use solution in a range that maintains the cells without harmful swelling or shrinking. An osmolality range can be between about 250 mOsM and about 350 mOsM, and can be between about 290 mOsM and about 320 mOsM. In general, the components of the use solution can be adjusted to achieve the desired range of osmolality.

If the semen extender composition is provided as a concentrate, it is expected that the amount of water provided in the use solution will be sufficient to keep the components of the semen extender composition in solution. It is believed that this amount of water is at least about 15 wt. %, and more preferably at least about 30 wt. %.

The semen extender composition includes an effective amount of phospholipids to protect the sperm cells introduced into the semen extender composition. In general, it is expected that the phospholipids will provide reduced ice-crystal formation and help stabilize the cell membrane. An exemplary source of phospholipids includes lecithin. The phospholipids can be obtained from a non-animal source. An exemplary type of non-animal lecithin that can be used is soy lecithin. In certain soy lecithin commercial products, it is believed that the lecithin contains about 60 wt. % phospholipids. It is believed that enzymatically treated lecithin is a type of lecithin that can be used according to the invention. Alternative phospholipids that can be used include phospholipids obtained from an animal source such as egg yolks.

The semen extender composition preferably includes a sufficient amount of phospholipids to provide the desired protectant properties. In general, it is expected that the semen extender composition will include at least about 0.1 wt. % phospholipids in order to provide the desired protectant properties. In addition, it is believed that adding too much phospholipids may be detrimental to protecting the cells. Accordingly, it is expected that the semen extender composition will include less than about 6 wt. % phospholipids. The semen extender composition can include between about 0.3 wt. % and about 3 wt. % lecithin, and can include between about 0.5 wt. % and about 1.5 wt. % phospholipids. It should be appreciated that the amount of phospholipids in the extender can be characterized by the amount of lecithin provided in the extender. The extender can include between about 0.1 wt. % and about 8 wt. % lecithin.

The semen extender composition can include carbohydrates for providing energy for the sperm cells. The carbohydrate can be preferably a simple metabolizable sugar that the cells can utilize for energy. Exemplary carbohydrates include fructose, glucose, and lactose. The carbohydrates can be used alone or in combination. The carbohydrate can be provided in the semen extender composition use solution in an amount sufficient to provide the cells with energy. It is expected that this amount is at least about 0.5 wt. %. If there is too much of the carbohydrate, it is expected that the osmolality of the composition may move to outside the desired range. Accordingly, it is expected that the carbohydrate will be provided in an amount of less than about 3 wt. %. An exemplary amount of carbohydrate source is between about 0.8 wt. % and about 1.5 wt. %.

The semen extender composition can include a surfactant to help reduce ice crystal growth during the freezing process and to help strengthen the cell membrane during the freezing and thawing process. Surfactants that can be used according to the invention include those surfactants that are considered to be sufficiently gentle so that they do not dissolve sperm cell membrane when used in an amount sufficient to reduce ice crystal formation and strengthen the cell membrane during the freezing and thawing process. Surfactants that are sufficiently gentle can include anionic surfactants, cationic surfactants, nonionic surfactants, amphoteric surfactants, and zwitterionic surfactants. Exemplary anionic surfactants that can be used include sulfates such as sodium lauryl sulfate and sodium laureth sulfate. Exemplary nonionic surfactants that can be used in the semen extender composition include sorbitan esters, glycerol esters, and polyglycerol esters. An exemplary type of sorbitan ester includes polyoxyethylene sorbitan monooleate. A preferred polyoxyethylene sorbitan monooleate is available under the name Tween 80 from Sigma Chemical Company. Additional surfactants that can be used according to the invention include phospholipids such as glycerophospholipids and sphingolipids.

The semen extender composition can include a single surfactant or a mixture of surfactants. The amount of surfactant provided in the extender can vary depending upon the detergency of the surfactant and the amount of phospholipids provided in the composition. In general, there should be sufficient amount of surfactant to reduce ice crystal formation and/or to preserve the cell membrane stability. It is believed that much more of the glycerol ester can be added compared with the polyoxyethylene sorbitan monooleate to provide the desired properties. It is expected that the semen extender composition use solution will include between about 0.0001 wt. % and about 1 wt. % surfactant, and more preferably between about 0.001 wt. % and about 0.1 wt. % surfactant. In the case of polyoxyethylene sorbitan monooleate, it is expected that this surfactant can be provided in an amount of between about 0.001 wt. % and about 0.005 wt. %.

The semen extender composition can be biologically buffered so that the use solution exhibits a pH that maintains the viability of the cells. The use solution can exhibit a pH of between about 6.9 and about 7.5. Commonly used biological buffers are available under the names TRIS, HEPES, and TES from Sigma Chemical Company. The amount of biological buffer provided in the use solution depends on the strength of the biological buffer and the desired buffering capacity of the use solution. In general, it is expected that the molar concentration of the biological buffer in the use solution is between about 0.05 M and about 0.25 M.

The semen extender composition can include antioxidants. Exemplary antioxidants include vitamin E, vitamin C, vitamin A, BHA, BHT, and their derivatives. Preferably, the semen extender composition includes a sufficient amount of antioxidant to provide the desired benefit. In general, it is expected that the use solution will include at least about 1

IU/ml antioxidant, and can include at least about 5 IU/ml antioxidant. The use solution can include up to about 3 wt. % antioxidant, and can include between about 1 wt. % and about 3 wt. % antioxidant.

A freeze agent can be provided in the extender composition for reducing ice-crystal formation. Exemplary freeze agents include polyols, such as, glycerol, and dimethylsulfoxide (DMSO). The semen extender composition can include between about 3 wt. % and about 14 wt. % freeze agent, and can include between about 6 wt. % and about 7.5 wt. % freeze agent. It should be understood that exemplary freeze agents include those derived from an animal source and those derived from a non-animal source.

It should be understood that the freeze agent can be provided as part of the use solution or it can be added to the combination of the use solution and the cells. When the use solution is provided for use by the one-step process, it is expected that the buffered ejaculate will be added directly to the use solution. In this case, the freeze agent will be provided as part of the use solution prior to adding the buffered ejaculate. As part of the two-step process, it is expected that the buffered ejaculate will be added to a use solution that does not contain a freeze agent, and then the freeze agent can be added to the combination of the use solution and the ejaculate.

The semen extender composition can include pH adjusters to provide the use solution with the desired pH. Exemplary pH adjusters that can be used according to the invention include any compatible weak acid or weak base. Exemplary pH adjusters include citric acid, lactic acid, pyruvic acid, and TRIS.

The semen extender composition can include a membrane stabilizing agent for stabilizing the membrane of the sperm cells. Exemplary stabilizing agents that can be used include cholesterol-cyclodextrin inclusion complex and stilbesterol. In general, these agents can be referred to as cholesterol-like stabilizing agents. Stilbesterol is preferred because it can be obtained from plant origin. The membrane stabilizing agent is preferably provided in an amount that provides for stabilization of the cell membrane relative to the absence of the agent.

Antibiotics can be included in the semen extender composition. Various antibiotics that can be used include well known antibiotics. Exemplary antibiotics include Gentamycin, Tylosin, Lincomycin, and Spectinomycin available from Sigma Chemical Company. The antibiotics can be used alone or in combination. It is expected that the antibiotics can be provided in a concentration of between about 5 mg/100 ml and about 30 mg/100 ml.

Two exemplary techniques for using the semen extender composition include a one-step method and a two-step method. The one-step method includes introducing harvested cells into the semen extender composition use solution and freezing the combination of semen extender use solution and harvested cells. The semen extender composition used in the one-step process preferably includes a freeze agent. The two-step process includes harvesting the cells, introducing the cells into a semen extender composition that does not include a freeze agent, cooling the combination of semen extender composition and cells, mixing in the freeze agent, and then freezing the composition. If desired, a freeze agent can be added.

It is generally desirable for the semen extender composition according to the invention to provide sperm cells having a desired level of viability and motility of at least about two hours after thaw. It is even more preferable to provide a desired level of viability and motility six hours after thaw. In general, a desired level of viability corresponds to a viability of at least 40% of the initial viability, and a desired level of motility corresponds to a level of at least 40% of the initial motility. Even more preferably, the levels of viability and motility are at least about 70% of the initial values. The components of the semen extender composition according to the invention can be selected to help maintain viability and motility of the sperm cells.

The following examples demonstrate formulations and uses of semen extender compositions according to the invention.

EXAMPLE 1

Semen was collected by rectal probe electro stimulation (electro ejaculation) from 66 gaur (*Bos gaurus*) after immobilization with carfentanil/xylazine, and 11 African buffalo (*Syncerus caffer*) after immobilization with etorphine/xylazine using a standard bovine protocol. Within 2 hours, sperm characteristics were recorded and the raw ejaculates divided into two cryopreservation groups: 1) a TRIS-citrate-egg yolk-based cryodiluent containing 7% glycerol (standard method), and 2) a soy-based cryodiluent containing 8% glycerol. The raw semen was first diluted (1:1) at room temperature in cryodiluent without glycerol, then refrigerated for 1 hour before slowly adding the cooled, glycerated cryodiluent. Semen treatments were loaded into 0.5 mL straws, then refrigerated an additional 2 hours before freezing in liquid $N_2$ vapor (2.5 cm above surface) for 10 min before plunging into the liquid $N_2$. The straws were thawed in a 32° C. water bath, then examined for overall percentage motility and kinetic rating (rate of forward progression with 0=no movement to 5=fast, linear movement) for the motility index (MI; actual % motility×kinetic rating/100).

TABLE 1

Means ± SEM for raw and cryopreserved semen from gaur and buffalo using a standard egg yolk-based cryodiluent versus a novel, soy-based cryodiluent

| | Gaur (n = 6) | | | Buffalo (n = 11) | | |
|---|---|---|---|---|---|---|
| | % Motility | | | % Motility | | |
| | Actual | Adjusted* | MI | Actual | Adjusted* | MI |
| Pre-freeze, raw semen | 69.2 ± 2.5[a] | 100[a] | 1.8 ± 0.1[a] | 81.2 ± 0.9[a] | 100[a] | 3.3 ± 0.1[a] |
| Thawed soy-based | 52.3 ± 3.6[b] | 72.2 ± 2.7[b] | 1.4 ± 0.1[a] | 70.7 ± 1.2[b] | 86.6 ± 0.9[b] | 2.2 ± 0.1[b] |
| Thawed egg yolk-based | 42.3 ± 3.5[c] | 60.7 ± 4.1[c] | 1.0 ± 0.1[a] | 65.9 ± 0.9[c] | 81.4 ± 0.8[c] | 1.7 ± 0.1[c] |

*Motility percentages adjusted relative to initial (pre-freeze, raw semen) estimations.
[a-c]Different superscripts within columns indicate significant differences (P < 0.05; chi-square).

The IVF of in vitro-matured domestic bovine oocytes with cryopreserved *B. gaurus* sperm resulted in higher (P<0.05) penetration rates using the soy-based, versus the egg yolk-based, cryodiluents (52.2±2.8 versus 30.6±1.8, respectively). This study demonstrates an improvement of bovine sperm cryopreservation using a non-animal protein cryodiluent that can enhance the international transport of bovid semen while reducing the potential of disease transmission.

EXAMPLE 2

Before cryopreserving the semen, each sample was evaluated for percent motile, percent normal morphology, rate of forward progression, percent viability and concentration of sperm per ml ejaculate. Then those evaluations were used to determine the freezing ratio (semen:HEPES-TL or extender A) needed to freeze samples at a final concentration of $50 \times 10^6$ motile, normal sperm per ml. The following equation was used to determine the freezing ratio:

$$\frac{100 \times 10^6}{(\text{Conc./ml}; \times 10^6) \times (\% \text{ Motile}; 0.00) \times (\% \text{ NormalMorphology}; 0.00)}$$

Three different bases were evaluated: TRIS base, TES/TRIS base and HEPES/TRIS base. The TRIS base was made to follow the guidelines set by the Certified Semen Services. The TES/TRIS and HEPES/TRIS bases were formulated to contain the same buffering capabilities as the already established TRIS base. The bases were formulated as follows:

| TRIS Base | TES/TRIS Base | HEPES/TRIS Base |
|---|---|---|
| 2.42 gm % TRIS | 2.0164 gm % TRIS | 2.18 gm % TRIS |
| 1.38 gm % Citric Acid | 0.229 gm % TES | 0.238 gm % HEPES |
| 1.00 gm % Fructose | 1.209 gm % Citric Acid | 1.24 gm % Citric Acid |
| 6.14 % Glycerol | 1.00 gm % Fructose | 1.00 gm % Fructose |
|  | 6.14 % Glycerol | 6.14 % Glycerol |

All bases were adjusted with TRIS Buffer to pH 7.2 and the osmolality for each was taken. The TRIS Base osmolality ranged from 300-320 mOsM/kg.H2O (and averaged 317 mOsM/kg.H2O), the TES/TRIS Base osmolality was 312 mOsM/kg.H2O and the HEPES/TRIS Base osmolality was 325 MOsM/kg.H2O.

Three different types of soy lecithin were evaluated at varying concentrations. The different types of soy lecithin contained differences in phospholipid and fatty acid compositions. All three types of soy lecithin are produced by Archer Daniels Midland Company, Decatur, Ill., USA. The different lecithin products are listed below followed by the concentration ranges they were tested at:

| 1) | Perfomix E (TG-069) | poor solubility in water |
|---|---|---|
| 2) | Yelkinol AC (UF-014) | 0.5% to 10% (v/v) |
| 3) | Ultralec P (UH-575) | 0.5% to 2% (v/v/) |

Soy lecithin was prepared in a 10% stock solution. The amount of lecithin powder needed was added to approximately 75% of the total volume of water needed. The mixture was homogenized 5-10 minutes to mix thoroughly, and then water was added to bring solution up to correct volume.

Three surface active agents were evaluated for improving the extender. The three surface active agents evaluated are listed below followed by the concentration ranges they were tested at:

| 1) | Cholesterol-cyclodextrin inclusion complex | 0.01 to 2.5 mg/ml |
|---|---|---|
| 2) | Sodium lauryl sulfate (Equex Paste) | 0.01% to 1.0% (v/v) |
| 3) | Polyoxyethylene sorbitan monooleate (Tween 80) | 0.02 to 2 mg/ml |

The surface active agent identified as cholesterol-cyclodextrin inclusion complex was prepared as described in the article "Alteration of the Myometrial Plasma Membrane Cholesterol Content with β-Cyclodextrin ModulaTES the Binding Affinity of the Oxytocin Receptor," by U. Klein, G. Gimpl, & F. Farehnolz, Biochemistry 1995:34:13784-13793.

The final addition tested was the antioxidant Vitamin E from five to 50 international units/ml.

Extenders were tested with semen samples using both one-step and two-step freezing methods.

For the one-step freezing method, the freezing ratio determined was diluted with HEPES-TL (BioWhittaker, U.S.A.). Then it was placed in a container of 35° C. water in an insulated container with warm packs around them until transported back to the lab (approximately 30-45 min). Once back at the lab, extender B (extender containing 12.3% glycerol) was added very slowly (drop by drop, while swirling) at room temperature, at a 1:1 dilution ratio (extender B:sperm+HEPES-TL). Then it was loaded into pre-labeled 0.5 ml straws, sealed with PVP sealing powder and refrigerated at 4° C. for two hours before freezing.

For the two-step freezing method, the freezing ratio determined was diluted with extender A, instead of HEPES-TL. It was placed in a beaker of 35° C. water in a cooled equitainer, or an insulated container with cold packs around the beaker, until transported back to the lab. Once back in the lab, the beakers containing the samples were placed in the refrigerator (4° C.) to cool. The samples were cooled at 4° C. for a total of two hours from the time they were placed into the equitainer or insulated cooler. At the same time, extender B, pre-labeled 0.5 ml straws, transfer pipettes and the PVP sealing powder were also placed in the refrigerator to cool.

After two hours of refrigeration (4° C.), the pre-cooled extender B was added very slowly (drop by drop), while gently mixing the sample, using a pre-cooled transfer pipette. Extender B was added at a 1:1 ratio (extender B:extended semen) for a final cryoprotectant concentration of 6.14% glycerol (v/v). After extender B was added, the samples were loaded into pre-labeled 0.5 ml straws and sealed with PVP powder (all occurred at 4° C.). Then the samples were refrigerated (4° C.) for an additional hour before freezing.

Straws for both the one-step and two-step methods were frozen the same way. The straws were placed directly on top of a block of dry ice contained in an insulated container (e.g. styrofoam) in the refrigerator for a minimum of 10 min (max 30 min). After a minimum of 10 min, the straws were plunged quickly into liquid nitrogen. If dry ice was not available, liquid nitrogen vapors were used. For this method the straws were placed on a rack exactly one inch above the surface of the liquid nitrogen for 10 min before being plunged. This also occurred in an insulated container. Once straws were plunged they were loaded into goblets and canes.

The straws were thawed by removing them from liquid nitrogen, directly and quickly, into a 30-33° C. water bath for 2-1½ min, while continuously stirring. The outside wall of the straws was then wiped off to remove any excess water and then the straws were decanted into a 1.5 ml microcentrifuge tube. The samples were mixed thoroughly, by gently pipetting. Then 0.1 ml of extended semen was diluted with 0.5 ml of pre-warned HEPES-TL in another microcentrifuge tube so that the sperm could be evaluated post-thaw.

After thawing, the motility and viability of the frozen semen was determined. For motility, small aliquots (i.e. 10 μl) were examined immediately post-thaw and at 2 hours post-thaw after allowing the samples to warm at 36-38° C. for 5-10 min. For viability, samples were examined with eosin B-fast green vital staining technique, by Aalseth and Saacke (Gamete Research 15:38-81, 1986).

Initially, three different bases were compared with a known bovine extender, available under the name Biladyl A. The following tables show how the bases with egg yolk compared to Biladyl A with egg yolk. The tables also show how each of the three bases with 1% soy lecithin (v/v) compared to each other.

TABLE 2

| 1 Step Freezing Method Extender | % Motile ± Standard 0 hours | Deviation Post-Thaw 2 hours | n values |
|---|---|---|---|
| Biladyl w/Egg Yolk | 45 ± 3 | 27 ± 4 | 2 |
| HEPES/TRIS w/Egg Yolk | 50 ± 0 | 14 ± 0 | 1 |
| TRIS w/Egg Yolk | 61 ± 22 | 31 ± 18 | 5 |
| TES/TRIS w/Egg Yolk | 43 ± 0 | 21 ± 0 | 1 |
| HEPES/TRIS w/1% Lecithin | 49 ± 2 | 31 ± 10 | 2 |
| TRIS w/1% Lecithin | 63 ± 27 | 40 ± 1 | 2 |
| TES/TRIS w/1% Lecithin | 43 ± 0 | 21 ± 0 | 1 |

TABLE 3

| 2 Step Freezing Method Extender | % Motile ± Standard 0 hours | Deviation Post-Thaw 2 hours | n values |
|---|---|---|---|
| Biladyl w/Egg Yolk | 60 ± 18 | 42 ± 17 | 8 |
| HEPES/TRIS w/Egg Yolk | 51 ± 23 | 35 ± 14 | 8 |
| TRIS w/Egg Yolk | 73 ± 25 | 48 ± 20 | 8 |
| TES/TRIS w/Egg Yolk | 56 ± 22 | 37 ± 12 | 8 |
| HEPES/TRIS w/1% Lecithin | 46 ± 21 | 32 ± 20 | 8 |
| TRIS w/1% Lecithin | 53 ± 25 | 42 ± 17 | 8 |
| TES/TRIS w/1% Lecithin | 39 ± 21 | 27 ± 14 | 8 |

Results show that TRIS w/Egg Yolk was the best base tested. The results from the bases with soy lecithin did not show an extender that was better. However, it did show that the TRIS base was a little better than the other two bases when used with soy lecithin.

After the optimum base was determined, we moved on to determine the optimum type and concentration of soy lecithin was evaluated. Performix E lecithin was not used because it was found to have poor solubility in water. Yelkinol AC lecithin was tested at 0.5, 1.0, 1.5, 2.0, 4.0, 5.0, 7.5 and 10% (v/v). Ultralec P lecithin was tested at 1.0, 1.5 and 2.0% (v/v). The following tables and FIGS. 1-6 show both types of lecithin around their determined optimum concentrations and how they compare to each other for both freezing methods at 0 and 2 hours post-thaw.

TABLE 4

| 1 Step Freezing Method Extender | % Motile ± Standard 0 hours | Deviation Post-Thaw 2 hours |
|---|---|---|
| 0.5% Yelkinol AC | 43 ± 15 | 32 ± 16 |
| 1.0% Yelkinol AC | 41 ± 24 | 27 ± 11 |
| 1.5% Yelkinol AC | 43 ± 0 | 29 ± 0 |
| 1.0% Ultralec P | 29 ± 8 | 16 ± 6 |
| 1.5% Ultralec P | 41 ± 17 | 27 ± 13 |
| 2.0% Ultralec P | 31 ± 0 | 19 ± 0 |

TABLE 5

| 2 Step Freezing Method Extender | % Motile ± Standard 0 hours | Deviation Post-Thaw 2 hours |
|---|---|---|
| 0.5% Yelkinol AC | 51 ± 21 | 38 ± 18 |
| 1.0% Yelkinol AC | 52 ± 20 | 37 ± 17 |
| 1.5% Yelkinol AC | 50 ± 17 | 35 ± 10 |
| 2.0% Yelkinol AC | 20 ± 4 | 14 ± 4 |
| 1.0% Ultralec P | 54 ± 17 | 40 ± 17 |
| 1.5% Ultralec P | 60 ± 14 | 46 ± 16 |
| 2.0% Ultralec P | 49 ± 17 | 42 ± 17 |

The Two-Step Freezing Method results show that 1.5% Ultralec P soy lecithin is the best concentration. The One-Step Freezing Method results show that there is really no difference between Yelkinol AC at 0.5, 1.0 or 1.5% and that Ultralec P is optimal at 1.5%. Therefore, we chose 1.5% Ultralec P soy lecithin for the optimum lecithin type and concentration because it was significantly better than any other concentration for the two-step freezing method at both zero and two hours post-thaw.

Once the optimum base and lecithin concentration were determined we looked at possible additives that would improve the performance of the extender. First, we looked at surface active agents, such as cholesterol-cyclodextrin inclusion complex, sodium lauryl sulfate (EQ) and polyoxyethylene sorbitan monooleate (Tween 80). The surfactants were also looked at in several combinations with each other. First we looked at sodium lauryl sulfate at concentrations ranging from 0.01% to 1.0% (v/v) and determined that the optimum concentration of sodium lauryl sulfate was 0.1% (v/v). Then we looked at varying concentrations of the cholesterol-cyclodextrin complex from 0.01 mg/ml to 2.5 mg/ml with and without sodium lauryl sulfate. From these tests we determined that the optimum range for the cholesterol-cyclodextrin inclusion complex was 0.01 mg/ml to 0.25 mg/ml.

Figure 1A:
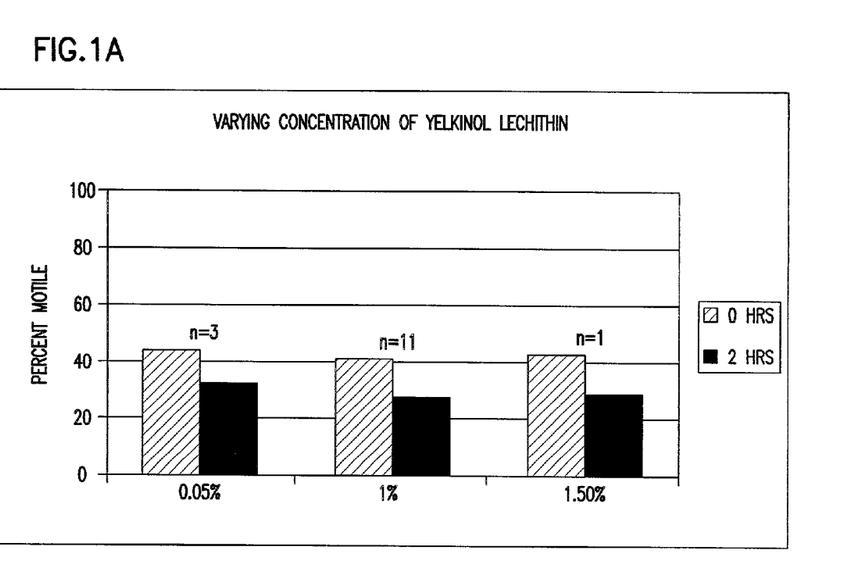
FIGS. 1(a) and 1(b) are graphical representations of percent motile sperm as a function of lecithin concentration (Yelkinol and Ultralec) in TRIS base in a one-step method for experimental data presented in Example 2.
Figure 1B:
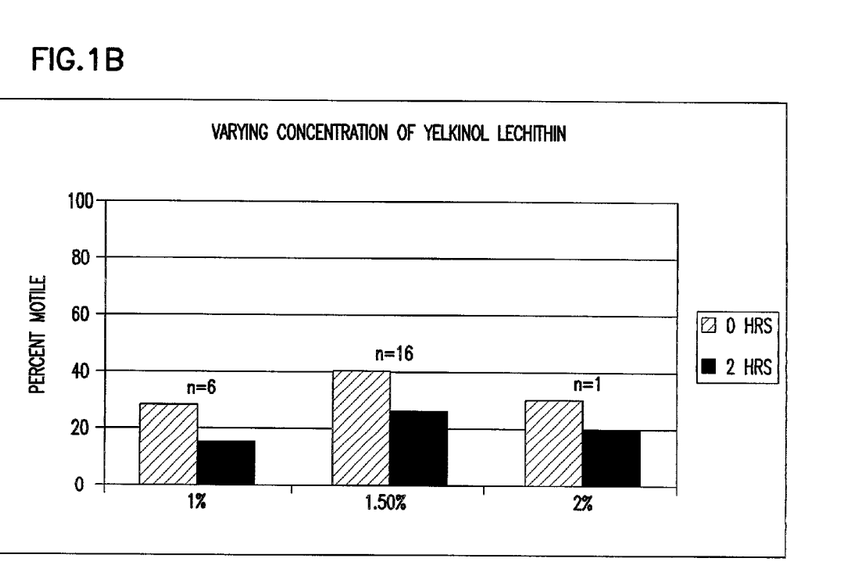
Figure 2A:
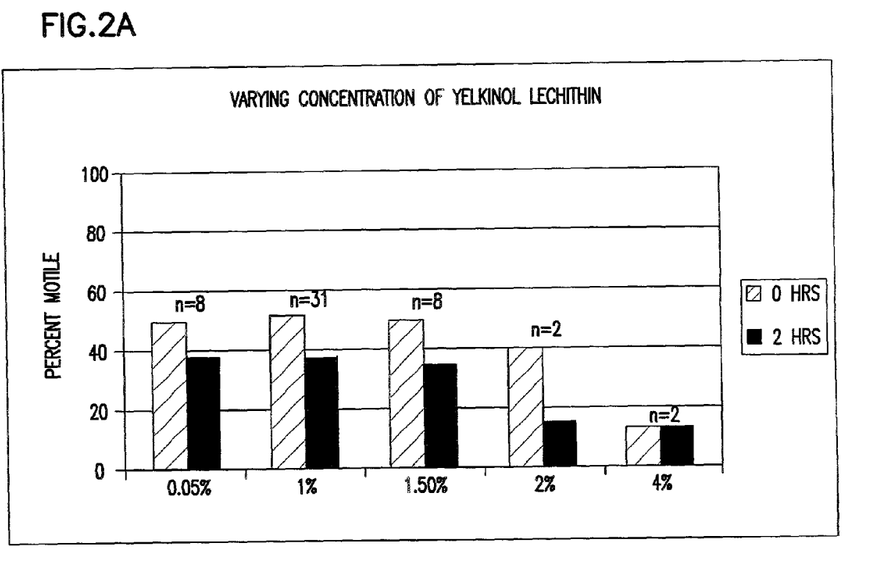
FIGS. 2(a) and 2(b) are graphical representations of percent motile sperm as a function of lecithin concentration (Yelkinol and Ultralec) in TRIS base in a two-step method for experimental data presented in Example 2.
Figure 2B:
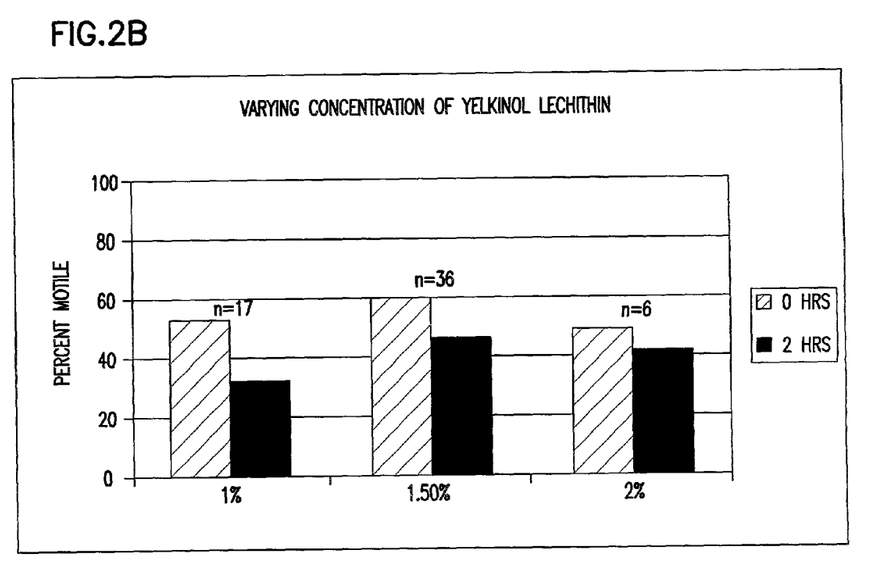
Figure 3:
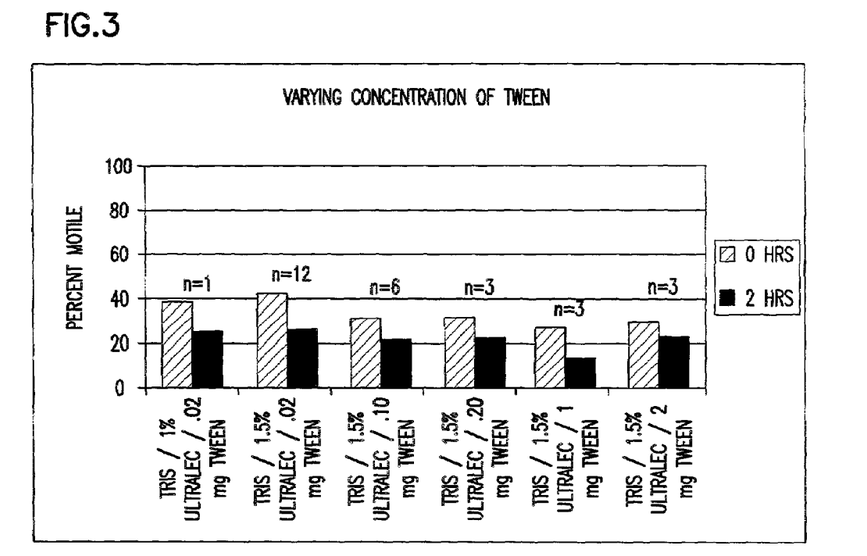
FIG. 3 is a graphical representation of percent motile sperm as a function of surfactant concentration (Tween 80) in TRIS base for a one-step method for experimental data presented in Example 2.
Figure 4:
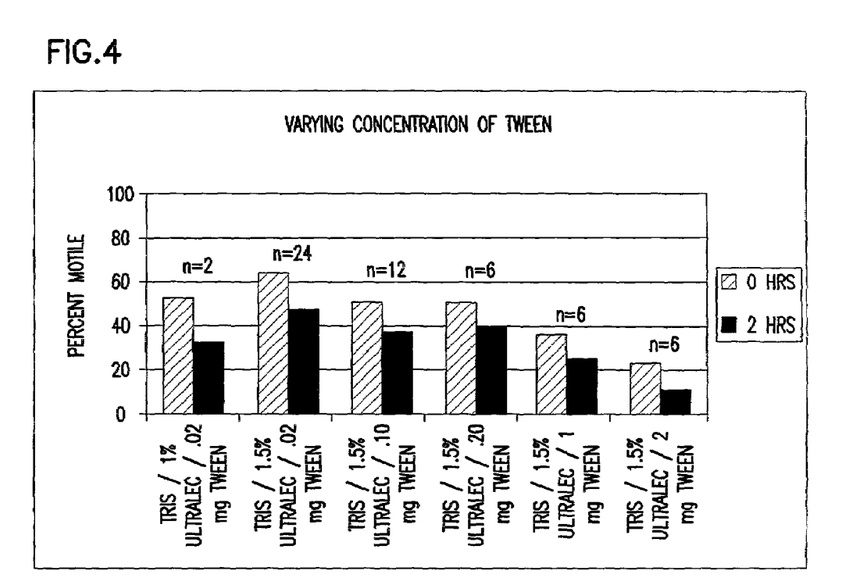
FIG. 4 is a graphical representation of percent motile sperm as a function of surfactant concentration (Tween 80) in TRIS base for a two-step method for experimental data presented in Example 2.

We tried polyoxyethylene sorbitan monooleate (Tween 80) as an additive. We chose Tween 80 because it is found in Tissue Culture Media 199 for embryos and believed it would not harm the bovine sperm. Tween 80 is found in TCM199 at 0.02 mg/ml, therefore we looked at Tween 80 concentrations ranging from 0.02 mg/ml to 2.0 mg/ml. FIGS. 3 and 4 and Tables 6 and 7 show post-thaw motility rates for polyoxyethylene sorbitan monooleate.

TABLE 6

| 1 Step Freezing Method Extender | % Motile ± Standard 0 hours | Deviation Post-Thaw 2 hours |
|---|---|---|
| TRIS/1% Lec/.02 mg Tween 80 | 38 ± 0 | 25 ± 0 |
| TRIS/1.5% Lec/.02 mg Tween 80 | 41 ± 10 | 26 ± 9 |
| TRIS/1.5% Lec/.10 mg Tween 80 | 31 ± 22 | 21 ± 16 |

TABLE 6-continued

| 1 Step Freezing Method Extender | % Motile ± Standard 0 hours | Deviation Post-Thaw 2 hours |
|---|---|---|
| TRIS/1.5% Lec/.20 mg Tween 80 | 31 ± 8 | 22 ± 13 |
| TRIS/1.5% Lec/1 mg Tween 80 | 28 ± 3 | 15 ± 7 |
| TRIS/1.5% Lec/2 mg Tween 80 | 29 ± 0 | 22 ± 2 |

TABLE 7

| 2 Step Freezing Method Extender | % Motile ± Standard 0 hours | Deviation Post-Thaw 2 hours |
|---|---|---|
| TRIS/1% Lec/.02 mg Tween 80 | 52 ± 6 | 32 ± 1 |
| TRIS/1.5% Lec/.02 mg Tween 80 | 64 ± 14 | 47 ± 14 |
| TRIS/1.5% Lec/.10 mg Tween 80 | 51 ± 16 | 37 ± 16 |
| TRIS/1.5% Lec/.20 mg Tween 80 | 51 ± 19 | 40 ± 20 |
| TRIS/1.5% Lec/1 mg Tween 80 | 36 ± 16 | 26 ± 19 |
| TRIS/1.5% Lec/2 mg Tween 80 | 23 ± 11 | 11 ± 3 |

The results show that 0.02 mg/ml polyoxyethylene sorbitan monooleate is the best concentration for one-step and two-step freezing methods at both 0 and 2 hrs post-thaw evaluation of percent motile.

Figure 5:
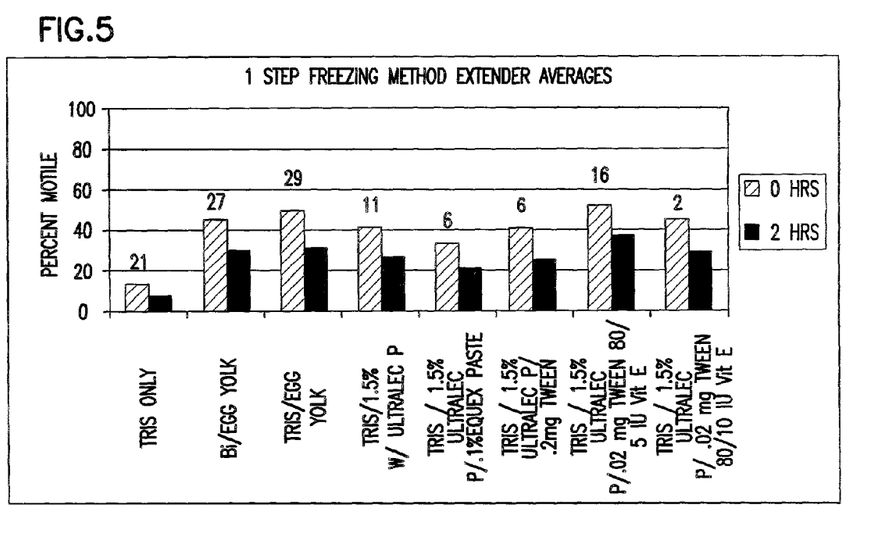
FIG. 5 is a graphical representation of percent motile sperm as a function of various semen extender compositions for one-step freezing method for experimental data presented in Example 2.
Figure 6:
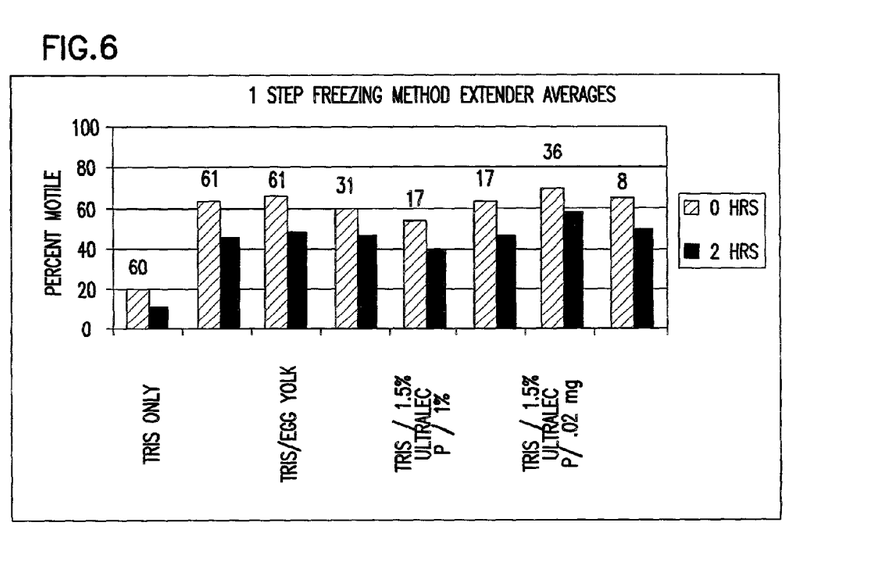
FIG. 6 is a graphical representation of percent motile sperm as a function of semen extender compositions for a two-step method for experimental data presented in Example 2.

The last additive we looked at was the antioxidant Vitamin E. Vitamin E was tested in extenders at 5 international units (IU), 10 IU and 50 IU/ml. Both 5 IU and 10 IU/ml showed improvement, however, 5 IU showed the most. FIGS. 5 and 6 and Tables 8 and 9 summarize the samples with several different extenders tested.

TABLE 8

| 1 Step Freezing Method Extender | % Motile ± Standard 0 hours | Deviation Post-Thaw 2 hours |
|---|---|---|
| TRIS Only | 13 ± 6 | 7 ± 2 |
| Biladyl A/Egg Yolk | 44 ± 13 | 30 ± 12 |
| TRIS/Egg Yolk | 50 ± 17 | 32 ± 14 |
| TRIS/1.5% Ultralec P | 41 ± 17 | 27 ± 13 |
| TPIS/1.5 Ultralec P/.1% Equex Paste | 34 ± 8 | 22 ± 7 |
| TRIS/1.5% Ultralec P/.02 mg Tween 80 | 41 ± 10 | 26 ± 9 |
| TRIS/1.5% Ultralec P/.02 mg Tween 80/5 IU Vit. E | 52 ± 13 | 38 ± 14 |
| TRIS/1.5% Ultralec P/.02 mg Tween 80/10 IU Vit. E | 46 ± 7 | 31 ± 14 |

TABLE 9

| 2 Step Freezing Method Extender | % Motile ± Standard 0 hours | Deviation Post-Thaw 2 hours |
|---|---|---|
| TRIS Only | 20 ± 9 | 11 ± 6 |
| Biladyl A/Egg Yolk | 63 ± 13 | 45 ± 14 |
| TRIS/Egg Yolk | 65 ± 15 | 47 ± 12 |
| TRIS/1.5% Ultralec P | 61 ± 14 | 46 ± 16 |
| TRIS/1.5 Ultralec P/.1% Equex Paste | 54 ± 14 | 39 ± 13 |
| TRIS/1.5% Ultralec P/.02 mg Tween 80 | 64 ± 14 | 47 ± 14 |
| TRIS/1.5% Ultralec P/.02 mg Tween 80/5 IU Vit. E | 69 ± 11 | 57 ± 13 |

TABLE 9-continued

| 2 Step Freezing Method Extender | % Motile ± Standard 0 hours | Deviation Post-Thaw 2 hours |
|---|---|---|
| TRIS/1.5% Ultralec P/.02 mg Tween 80/10 IU Vit. E | 64 ± 12 | 49 ± 12 |

The above specification, examples and data provide a complete description of the manufacture and use of the composition of the invention. Since many embodiments of the invention can be made without departing from the spirit and scope of the invention, the invention resides in the claims hereinafter appended.

We claim:

1. An aqueous ready to use semen extender composition comprising:
    (a) about 0.1 wt. % to about 6 wt. % phospholipid obtained from a non-animal source comprising lecithin;
    (b) about 0.0001 wt. % to about 1 wt. % of anionic surfactant to reduce ice crystal formation during freezing of the composition, wherein the anionic surfactant comprises a sulfate;
    (c) about 0.5 wt. % to about 3 wt. % carbohydrate;
    (d) about 3 wt. % to about 14 wt. % freeze agent comprising glycerol; and
    (e) biological buffer to provide the composition with a pH of about 6.9 to about 7.5,
and wherein the composition comprises a sufficient amount of water so that the composition exhibits an osmolality of about 250 mOsM to about 350 mOsM, wherein the composition is substantially free of animal products.

2. An aqueous ready to use semen extender composition according to claim 1, wherein the composition comprises at least about 90 wt. % water.

3. An aqueous ready to use semen extender composition according to claim 1, further comprising antioxidant.

4. An aqueous ready to use semen extender composition according to claim 3, wherein the antioxidant comprises at least one of vitamin E, vitamin C, vitamin A, BHA, EHT, or derivatives thereof.

5. An aqueous ready to use semen extender composition according to claim 1, wherein the anionic surfactant comprises at least one of sodium lauryl sulfate, sodium laureth sulfate, or mixtures thereof.

6. An aqueous ready to use semen extender composition according to claim 1, further comprising semen.

7. A method for manufacturing an aqueous ready to use semen extender composition, the method comprising a step of:
    (a) mixing semen extender composition components to provide a semen extender composition having an osmolality of about 250 mOsM to about 350 mOsM and a pH of about 6.9 to about 7.5, the semen extender composition components comprising:
        (i) about 0.1 wt. % to about 6 wt. % phospholipid obtained from a non-animal source comprising lecithin;
        (ii) about 0.0001 wt. % to about 1 wt,% of anionic surfactant to reduce ice crystal formation during freezing of the composition, wherein the anionic surfactant comprises a sulfate;

(iii) about 0.5 wt. % to about 3 wt.;
(iv) about 3 wt. % to about 14 wt. % freeze agent comprising glycerol;
(v) water; and
(vi) biological buffer) wherein the composition is substantially free of animal products.

8. An aqueous ready to use semen extender composition according to claim 1, wherein the composition further comprises at least about 1 IU/ml antioxidant.

9. An aqueous ready to use semen extender composition according to claim 1, wherein the composition further comprises at least about 5 IU/ml antioxidant.

10. An aqueous ready to use semen extender composition according to claim 1, wherein the composition further comprises about 1 wt. % to about 3 wt. % antioxidant.

11. A method according to claim 7, wherein the composition components further comprise at least about 1 IU/ml antioxidant.

12. A method according to claim 7, wherein the composition components further comprise at least about 5 IU/ml antioxidant.

13. A method according to claim 7, wherein the composition components further comprise about 1 wt. % to about 3 wt. % antioxidant.

14. A method according to claim 11, wherein the antioxidant comprises at least one of vitamin E, vitamin C, vitamin A, BHA, BHT, or derivatives thereof.

15. A method according to claim 7, wherein the anionic surfactant comprises at least one of sodium lauryl sulfate, sodium laureth sulfate, or mixtures thereof.

* * * * *